(12) United States Patent
Mancini et al.

(10) Patent No.: US 6,346,373 B1
(45) Date of Patent: Feb. 12, 2002

(54) WHOLE CELL ASSAY FOR CATHEPSIN K ACTIVITY

(75) Inventors: Joseph Mancini, Kirkland; Denis Riendeau, Pierrefonds; David Claveau, Montreal Nord, all of (CA)

(73) Assignee: Merck Frosst Canada & Co.,, Kirkland (CA)

( * ) Notice: Subject to any disclaimer, the term of this patent is extended or adjusted under 35 U.S.C. 154(b) by 0 days.

(21) Appl. No.: 09/553,724

(22) Filed: Apr. 20, 2000

Related U.S. Application Data

(60) Provisional application No. 60/132,625, filed on May 5, 1999.

(51) Int. Cl.[7] .................................................. C12Q 1/37
(52) U.S. Cl. .............................. 435/4; 435/24; 435/325
(58) Field of Search .......................... 435/23, 24, 7.21, 435/7.72, 325, 320.1, 29, 7.4, 455

(56) References Cited

U.S. PATENT DOCUMENTS

| | | | | |
|---|---|---|---|---|
| 4,902,509 A | * | 2/1990 | Turk et al. ................... | 424/105 |
| 5,736,357 A | * | 4/1998 | Bromme et al. ............ | 435/69.1 |
| 5,871,946 A | * | 2/1999 | Lucas et al. .................. | 435/18 |

FOREIGN PATENT DOCUMENTS

| | | | |
|---|---|---|---|
| WO | WO 96/13523 | * | 5/1996 |
| WO | WO 96 36729 | | 11/1996 |
| WO | WO 97 47642 | | 12/1997 |
| WO | EPO 861 898 | | 2/1998 |

OTHER PUBLICATIONS

Mancini, J.A., et al., FASEB Journal, vol. 13, No. 4, P.A1556, 1999.
McQueny, M., et al., Protein Expressions and Purification, vol. 14, pp 387–394, 1998.
Claveau, D., et al., Biochemical Pharmacology, vol. 60, pp 759–769, 2000.
Guay, J., et al., Bone, vol. 25, No. 2, pp 205–209, 1999.
McQueney, M.S., et al., "Autocatalytic Activation of Human Cathespin K", J. Biol Chem 272, pp 13955–13960, 1997.
Littlewood–Evans, A. et al., "Localization of Cathespin K in Human Osteoclasts by In Situ Hybridization and Immunohistochemistry", Bone 20, pp 81–86, 1997.
Bromme, D. et al., "Human Cathespin O2, Matrix Protein–degrading Cysteine Protease Expressed in Osteoclasts", J. Biol. Chem 271, pp 2126–2132, 1996.
Bossard, M.J. et al., "Proteolytic Activity of Human Osteoclast Cathespin K", J. Biol Chem 271, pp 12517–12524, 1996.
Bromme, D., et al.., "Peptidyl vinyl sulphones: a new class of potent and selective cysteine protease inhibitors", BioChem J. 315, pp 85–89, 1996.
Thompson, S.K., et al., "Design of potent and selective human cathespin K inhibitors that span the active site", Proc Natl Acad Sci USA 94, pp 14249–14254, 1997.
Nesbitt, S.A., et al., "Trafficking of Matrix Collagens Through Bone–Resorbing Osteoclasts", Science 276, pp 266–269, 1997.
Salo, J. et al., "Removal of Osteolcast BoneResorption Products by Transcytosis", Science 276, pp 270–273, 1997.
Mancini, et al., "Nitric Oxide Superoxide and Peroxynitrite Modulate Osteoclast Activity", Biochem Biophys Res Commun Feb 243 (3), pp 785–90, 1998.
Guo, et al., "Peptidyl N–Nitrosoanilines: A Novel Class of Cysteine Protease Inactivators", J.A.C.S. 120, pp 3726–3724, 1998.
Ralston, S.H., et al., "Nitric Oxide and Bone: What a Gas!", Br. J. Rheumatology 36, pp 831–838, 1997.
Shi et al. 1995. FEBS Letters 357:129–134.*
Duong et al. 1998. J. Clin. Invest. 102:881–892.*
Ariyoshi et al. 1998. Arterioscler. Thromb. Vasc. Biol. 18:493–498.*
New England Biolabs catalob, 1996–1997. Table of contents (pp. 2–3), and pp. 164–165.*

* cited by examiner

*Primary Examiner*—Robert A. Schwartzman
*Assistant Examiner*—Bronwen M. Loeb
(74) *Attorney, Agent, or Firm*—Nicole M. Wallinger; Melvin Winokur

(57) ABSTRACT

The present invention relates to a whole cell assay for cathepsin K. The present invention is useful for determining cathepsin K activity in a mammalian cell systems and for identifying and evaluating inhibitors of cathepsin K.

21 Claims, 9 Drawing Sheets

WHOLE CELL ASSAY FOR CATHEPSIN K ACTIVITY

This application claims the benefit of U.S. Provisional No. 60/132,625, filed May 5, 1999 Expired.

BRIEF DESCRIPTION OF THE INVENTION

The present invention relates to a whole cell assay for cathepsin K. The present invention is useful for determining cathepsin K activity in mammalian cell systems and for identifying and evaluating inhibitors of cathepsin K.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy, and multiple myeloma. One of the most common of these disorders is osteoporosis, which in its most frequent manifestation occur in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Osteoporosis is characterized by progressive loss of bone architecture and mineralization leading to the loss in bone strength and an increased fracture rate. The skeleton is constantly being remodeled by a balance between osteoblasts that lay down new bone and osteoclasts that breakdown, or resorb, bone. In some disease conditions and advancing age the balance between bone formation and resorption is disrupted; bone is removed at a faster rate. Such a prolonged imbalance of resorption over formation leads to weaker bone structure and a higher risk of fractures.

Bone resorption, is primarily performed by multinuclear giant cells, the osteoclasts. The mechanism by which osteoclasts resorb bone is by an initial cellular attachment to bone tissue followed by the formation of an extracellular compartment or lacunae. The lacunae are maintained at a low pH by a proton-ATP pump. The acidified environment allows for initial demineralization of bone followed by the degradation of bone proteins or collagen by proteases such as cysteine proteases (Delaisse, J. M. et al., 1980, *Biochem J* 192:365–368; Delaisse, J. et al., 1984, *Biochem Biophys Res Commun:*441–447; Delaisse, J. M. et al.,1987, *Bone* 8:305–313). Collagen constitutes 95% of the organic matrix of bone. Therefore, proteases involved in collagen degradation are an essential component of bone turnover, and the development and progression of osteoporosis.

Cathepsins belong to the papain superfamily of cysteine proteases. These proteases function in the normal physiological as well as pathological degradation of connective tissue. Cathepsins play a major role in intracellular protein degradation and turnover and remodeling. To date, a number of cathepsin have been identified and sequenced from a number of sources. These cathepsins are naturally found in a wide variety of tissues. For example, cathepsin B, F, H, L, K, S, W, and Z have been cloned. Cathepsin K (which is also known by the abbreviation cat K) is also known as cathepsin O and cathepsin O2. See, PCT Application WO 96/13523, Khepri Pharmaceuticals, Inc., published May 9, 1996.

Cysteine protease inhibitors such as E-64 (trans-epoxysuccinyl-L-leucylamide-(4-guanidino) butane) are known to be effective in inhibiting bone resorption (Delaisse, J. M. et al., 1987, *Bone* 8:305–313). Recently, cathepsin K was cloned and found specifically expressed in osteoclasts (Tezuka, K. et al., 1994, *J Biol Chem* 269:1106–1109; Shi, G. P. et al.,1995, *FEBS Lett* 357:129–134; Bromme, D. and Okamoto, K., 1995, *Biol Chem Hoppe Seyler* 376:379–384; Bromme, D. et al., 1996, *J Biol Chem* 271:2126–2132; Drake, F. H. et al., 1996,*J Biol Chem* 271:12511–12516). Concurrent to the cloning, the autosomal recessive disorder, pycnodysostosis, characterized by an osteopetrotic phenotype with a decrease in bone resorption, was mapped to mutations present in the cathepsin K gene. To date, all mutations identified in the cathepsin K gene are known to result in inactive protein (Gelb, B. D. et al., 1996, *Science* 273:1236–1238; Johnson, M. R. et al., 1996, *Genome Res* 6:1050–1055. Therefore, it appears that cathepsin K is probably involved in osteoclast mediated bone resorption.

Cathepsin K is synthesized as a 37 kDa pre-pro enzyme, which is localized to the lysosomal compartment and where it is presumably autoactivated to the mature 27 kDa enzyme at low pH (McQueney, M. S. et al., 1997, *J Biol Chem* 272:13955–13960; Littlewood-Evans, A. et al., 1997, *Bone* 20:81–86). Cathepsin K is most closely related to cathepsin S having 56% sequence identity at the amino acid level. The $S_2P_2$ substrate specificity of cathepsin K is similar to that of cathepsin S with a preference in the P1 and P2 positions for a positively charged residue such as arginine, and a hydrophobic residue such as phenylalanine or leucine, respectively (Bromme, D. et al, 1996, *J Biol Chem* 271: 2126–2132; Bossard, M. J. et al.,1996,) *J Biol Chem* 271:12517–12524). Cathepsin K is active at a broad pH range with significant activity between pH 4–8, thus allowing for good catalytic activity in the resorption lacunae of osteoclasts where the pH is about 4–5.

Human type I collagen, the major collagen in bone is a good substrate for cathepsin K (Kafienah, W., et al, 1998, *Biochem J* 331:727–732). In vitro experiments using antisense oligonucleotides to cathepsin K, have shown diminished bone resorption in vitro probably due to a reduction in translation of cathepsin K mRNA (Inui, T., et al., 1997, *J Biol Chem* 272:8109–8112. The crystal structure of cathepsin K has been resolved (McGrath, M. E., et al., 1997, *Nat Struct Biol* 4:105–109; Zhao, B., et al., 1997, *Nat Struct Biol* 4: 109–11) and selective peptide based inhibitors of cathepsin K have been developed (Bromme, D., et al., 1996, *Biochem J* 315:85–89; Thompson, S. K., et al., 1997, *Proc Natl Acad Sci U S A* 94:14249–14254). Analyses of these inhibitors should provide further evidence for the role of cathepsin K in bone resorption and in pathological disorders such as osteoporosis.

An in vitro model for bone resorption, is a pit formation assay in which purified osteoclasts are cultured on bone slices and resorbing activity is determined by measuring collagen degradation products using ELISA or by counting the number of pits formed (Nesbitt, S. A., and Horton, M. A., 1997, *Science* 276:266–269; Salo, J., et al., 1997, *Science*

276:270–273). It is thought that the cultured osteoclasts create tight junctions with bone matrix forming lacunae in which collagen is degraded, the degraded collagen is transcytosed through the osteoclasts. Drawbacks of this assay are; does not specifically measure cathepsin K activity, isolation of osteoclasts is long and difficult, quantitation of pits is variable and changes in pit area is not assessed.

In U.S. Pat. No. 5,871,946, there is described a method for determining the activity of enzymes in metabolically active whole cells in the absence of any genetic manipulations for the purpose of identifying abnormal cells. The enzymes described include different cathepsins. The patent teaches different reagents to be used for enzymatic substrates and the methods for making these reagents. However, this patent does not teach a specific genetically engineered cell-based assay for cathepsin K as a tool for identifying cell-permeable inhibitors of cathepsin K.

To date there are no known cell-based assays that specifically determine cathepsin K activity that can be used to identify cell-permeable inhibitors of cathepsin K and are amenable to high throughput screening. Therefore, one object of the present invention is to develop a cell-based assay specific to cathepsin K and devoid of the activity of other proteases. An additional object is to provide a cell-based assay specific to cathepsin K that can be easily scaled up for high throughput screening for screening and identifying inhibitors to cathepsin K. To that end, a stable cell line expressing cathepsin K and in which the pre-pro- enzyme is intracellularly processed to its mature and active form is provided.

The invention further provides cell permeable cathepsin K substrates, useful in measuring intracellular cathepsin K activity.

Another object is to provide a reliable and reproducible assay for cathepsin K using conditions in which extracellular protease activity is inhibited.

A further object of the present invention is to provide an assay for cathepsin K under reaction conditions favoring the measurement of intracellular cathepsin K activity. Such an assay can be scaled up for high throughput screening to identify inhibitors to cathepsin K.

These and other objects will become apparent to those of ordinary skill from the teachings provided herein.

The application refers to a number of publications, patents and patent applications the contents of which are hereby incorporated by reference in their entirety.

SUMMARY OF THE INVENTION

In one embodiment, the present invention relates to a method for assaying cathepsin K activity in a mammalian host cell, comprising the steps of:
a) transforming a host cell with a vector containing a nucleotide sequence encoding pre-pro-cathepsin K to provide a transformed host cell;
b) incubating said transformed host cell with a substrate to said cathepsin K; and
c) determining the cathepsin K activity in the transformed host cell.

Another embodiment of the present invention relates to a screening method for identifying a compound useful as an inhibitor of cathepsin K comprising the steps of:
a) incubating an eukaryotic host cell transformed with a vector containing a nucleotide sequence encoding pre-pro-cathepsin K with a substrate to the cathepsin K in the presence of said compound;
b) incubating an eukaryotic host cell transformed with a vector containing a nucleotide sequence encoding pre-pro-cathepsin K with a substrate to said cathepsin K in the absence of said compound;
c) comparing the cathepsin K activity of (a) to (b).

The present invention is further directed to expression vectors comprising a nucleotide sequence encoding cathepsin K and to recombinant host cells and cell lines comprising the said vector. The present invention further includes, assay kits for determining cathepsin K activity and high throughput screening systems for identifying inhibitors of cathepsin K.

All percentages and ratios used herein, unless otherwise indicated, are by weight. The invention hereof can comprise, consist of, or consist essentially of the essential as well as optional ingredients, components, and methods described herein.

DESCRIPTION OF THE FIGURES

FIG. 2A shows CHO/mock cells stained with a monoclonal antibody to cathepsin K.

FIG. 2B shows CHO/hCat K cells stained with a monoclonal antibody to cathepsin K.

FIG. 2C shows CHO/mock cells stained with a polyclonal antibody to cathepsin B.

Exposure of 2C is manually adjusted to the automatic setting obtained with 2B, and exposure of panel 2A is manually increased in comparison with exposures of 2B and 2C in order to detect the background level of fluorescence.

Figure 3B:
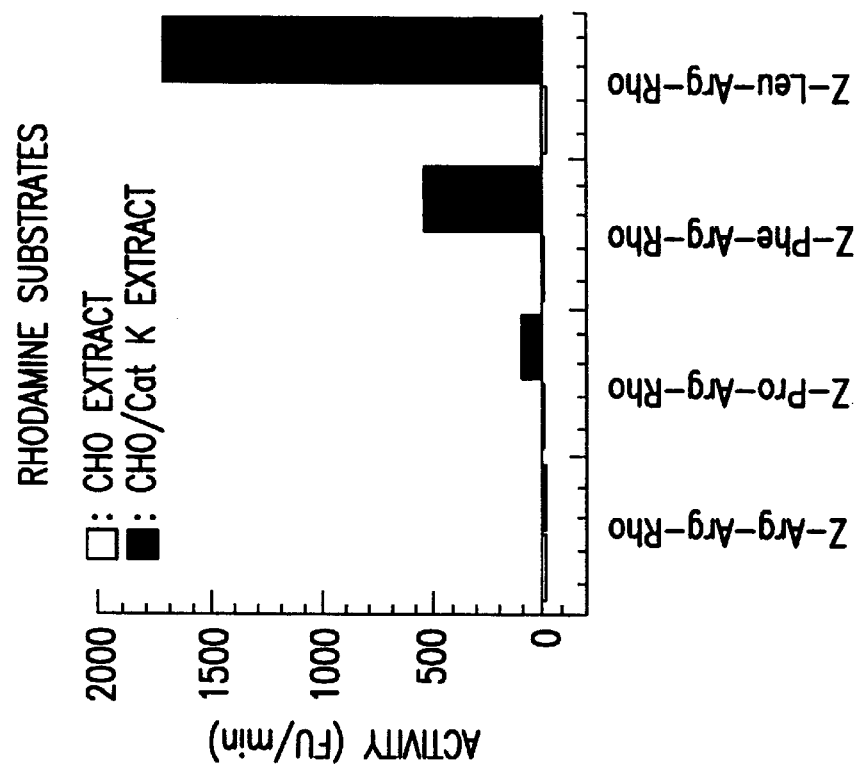
Figure 3A:
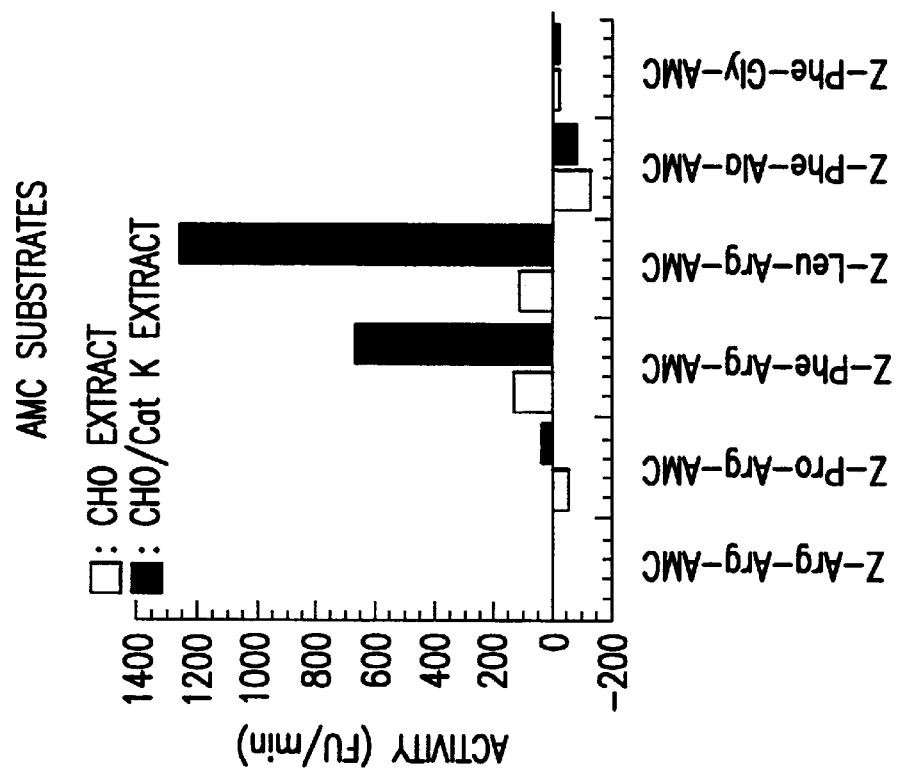

FIGS. 3A and 3B show the hydrolysis of fluorogenic di-peptide substrates by supernatant prepared from extracts of mock and hCat K expressing CHO cells. Supernatants are prepared as described above. Aliquotes of 1 µg/ml of total cell protein in 200 µl of buffer A, are incubated with 5 µM of a fluorogenic peptide substrate and the rate of substrate hydrolysis is determined. The reported enzymatic activities constitute the initial rate of substrate hydrolysis and each data point is an average of duplicates.

FIG. 3A shows the rate of hydrolysis using AMC conjugated substrates.

FIG. 3B shows the rate of hydrolysis using rhodamine conjugated substrates.

Figure 4:
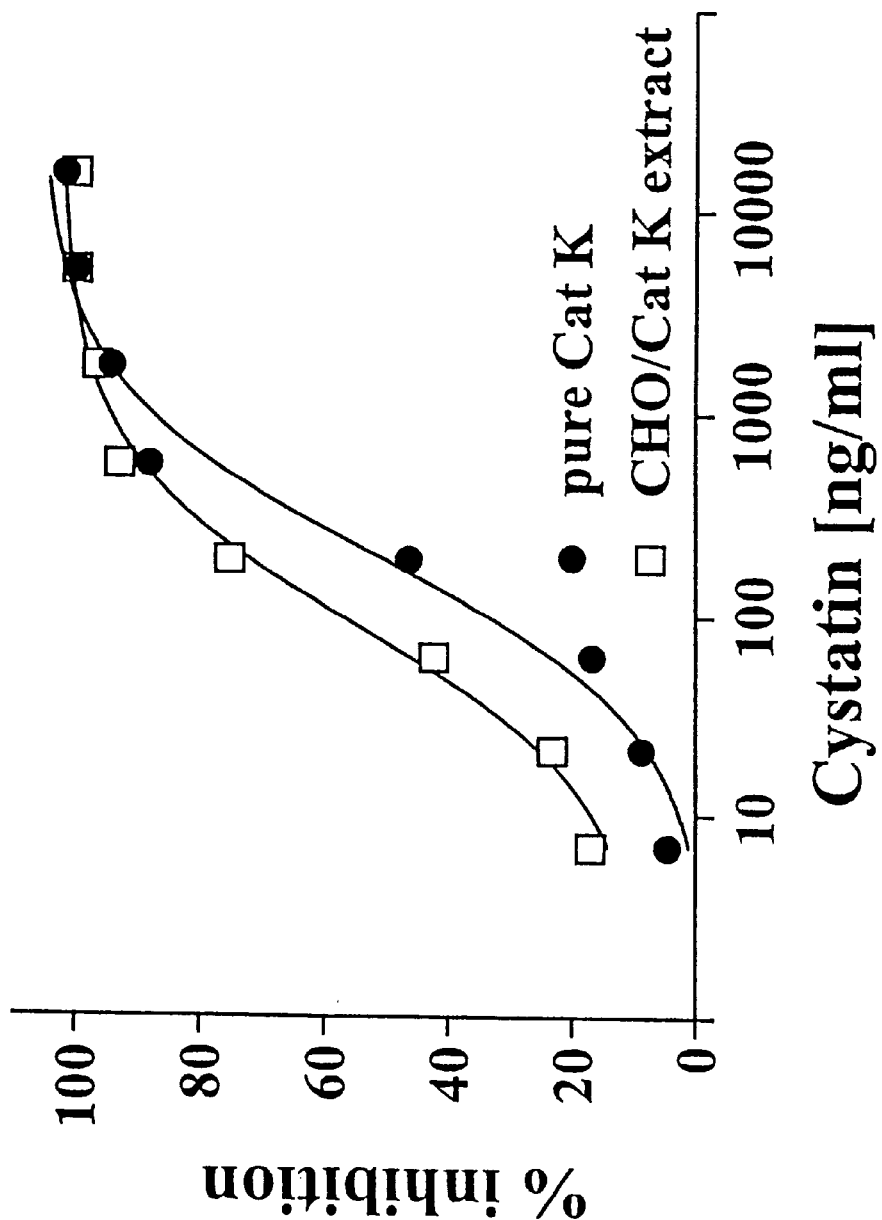

FIG. 4 shows the effect of cystatin on cathepsin K activity. The rate of substrate hydrolysis is determined in supernatants from extracts of mock and cathepsin K expressing cells (5 µg/ml of total cell protein in buffer A) and a suspension of pure cathepsin K enzyme (3 nM resuspended in buffer A), in the presence of different concentrations of cystatin. Suspensions are preincubated with cystatin for 15 min, then the reaction is initiated with the addition of the substrate (5 µM Z-Leu-Arg-Rhodamine). Each data point is an average of duplicates and is reported as a percentage of inhibition of the control reaction.

Figure 5:
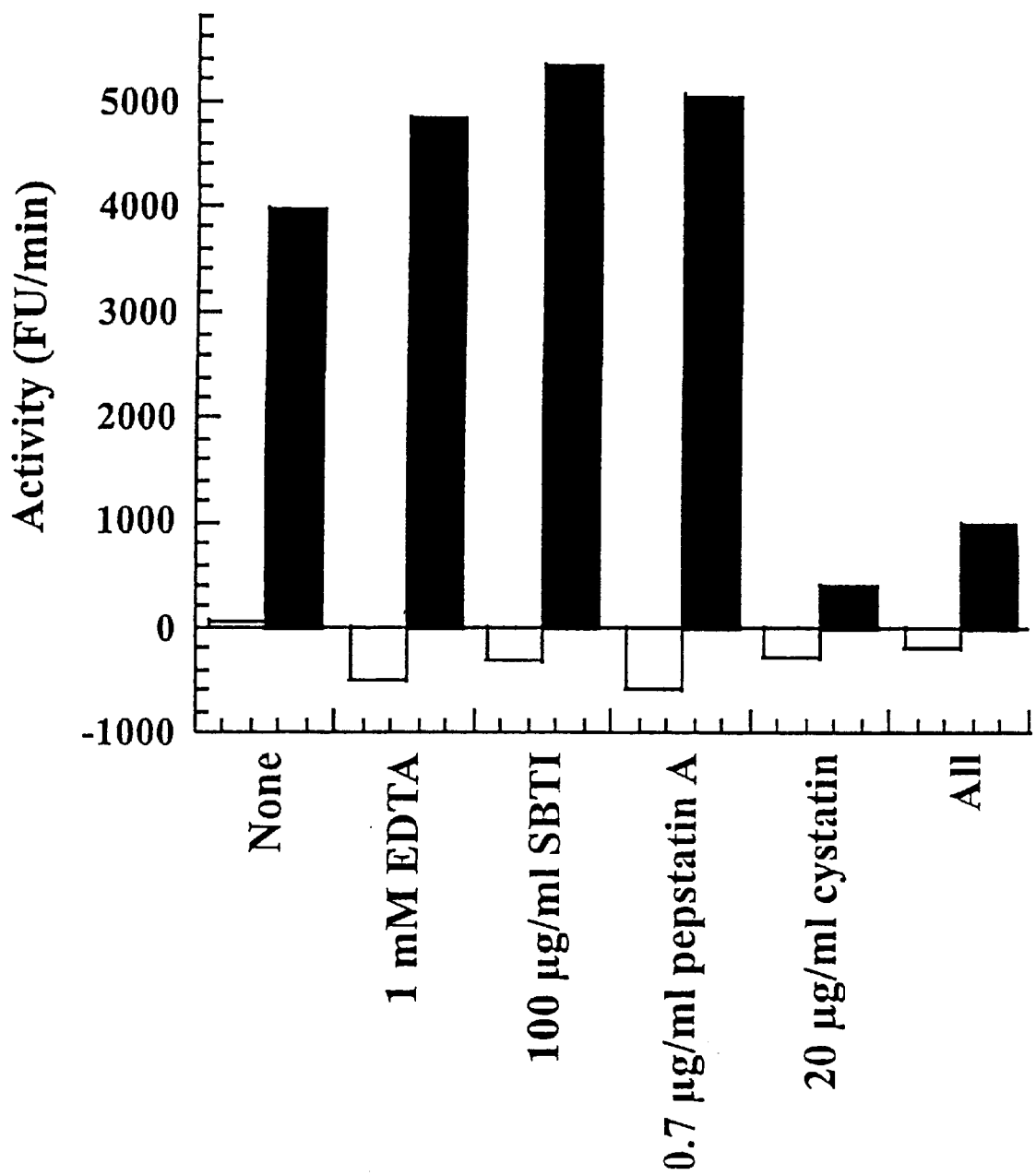

FIG. 5 shows the effect of various cell-impermeable protease inhibitors on the hydrolysis of Z-Leu-Arg-Rhodamine by mock (open bars) or hCat K (closed bars) expressing cells. Cells are seeded in sterile 96-wells cell culture plates, grown for 24 h and then washed twice with PBS. Into each well, HBSS pH 7.4 containing 15 mM Hepes is added. The rate of substrate hydrolysis is determined in the presence of the designated protease inhibitors. Cells are preincubated with an inhibitor for 15 min, then the reaction initiated with the addition of the substrate, 5 µM Z-Leu-Arg-Rhodamine. The results show that cystatin is an effective inhibitor of extracellular cathepsin K activity. The reported enzymatic activities constitute the initial rate of substrate hydrolysis and each data point is an average of duplicates.

Figure 6B:
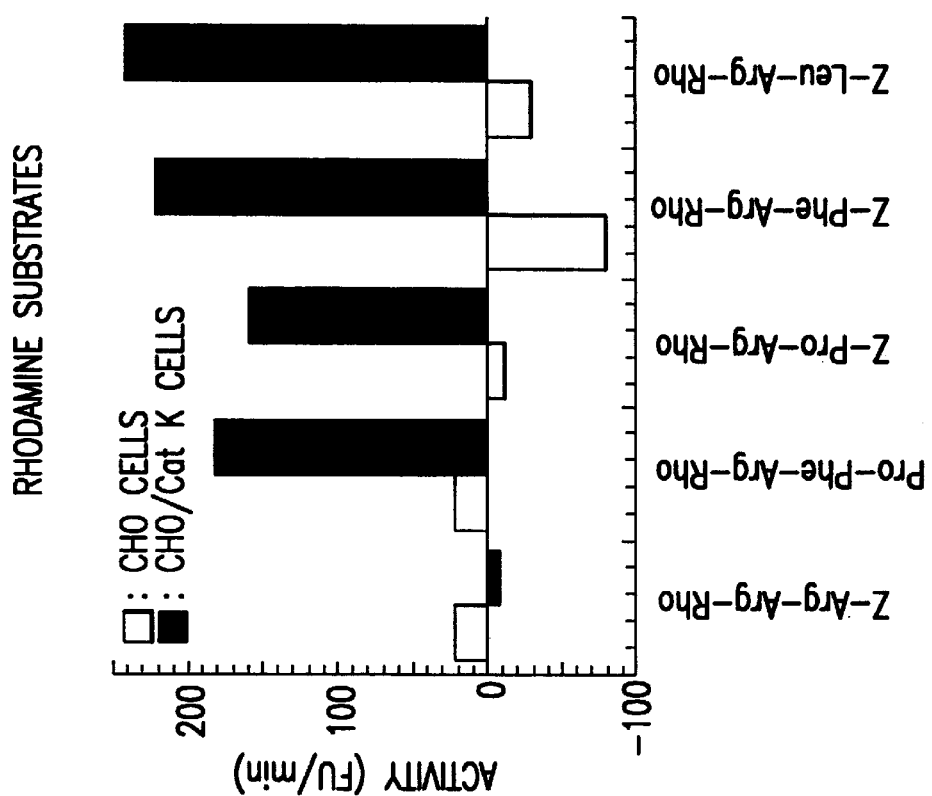
Figure 6A:
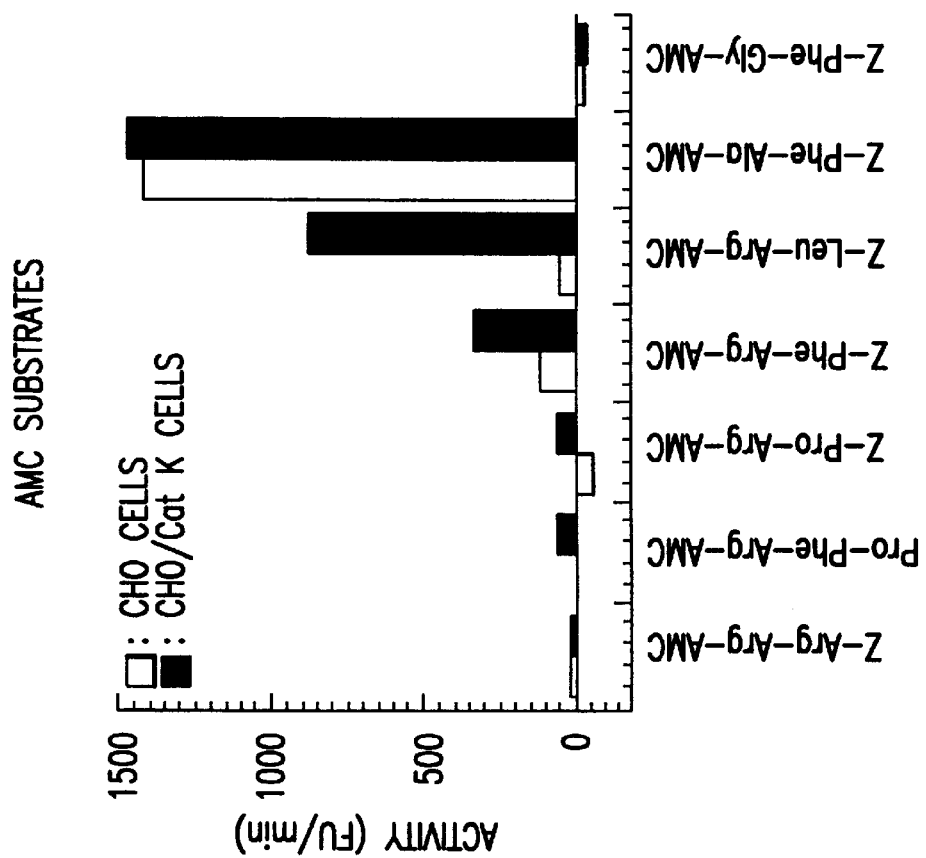

FIGS. 6A and 6B show the hydrolysis of fluorogenic di- and tri-peptide substrates by mock and hCat K expressing CHO cells. Cells are seeded in sterile 96-wells cell culture plates, grown for 24 h and washed twice with PBS. Into each well, HBSS pH 7.4 supplemented with 15 mM Hepes, 20 µg/ml cystatin and 100 µg/ml SBTI is added. After a 15 min preincubation, the reactions are initiated by the addition of 5 µM of the designated peptide substrates. The activities constitute the initial rate of substrate hydrolysis and each data point is an average of duplicates.

Figure 7:
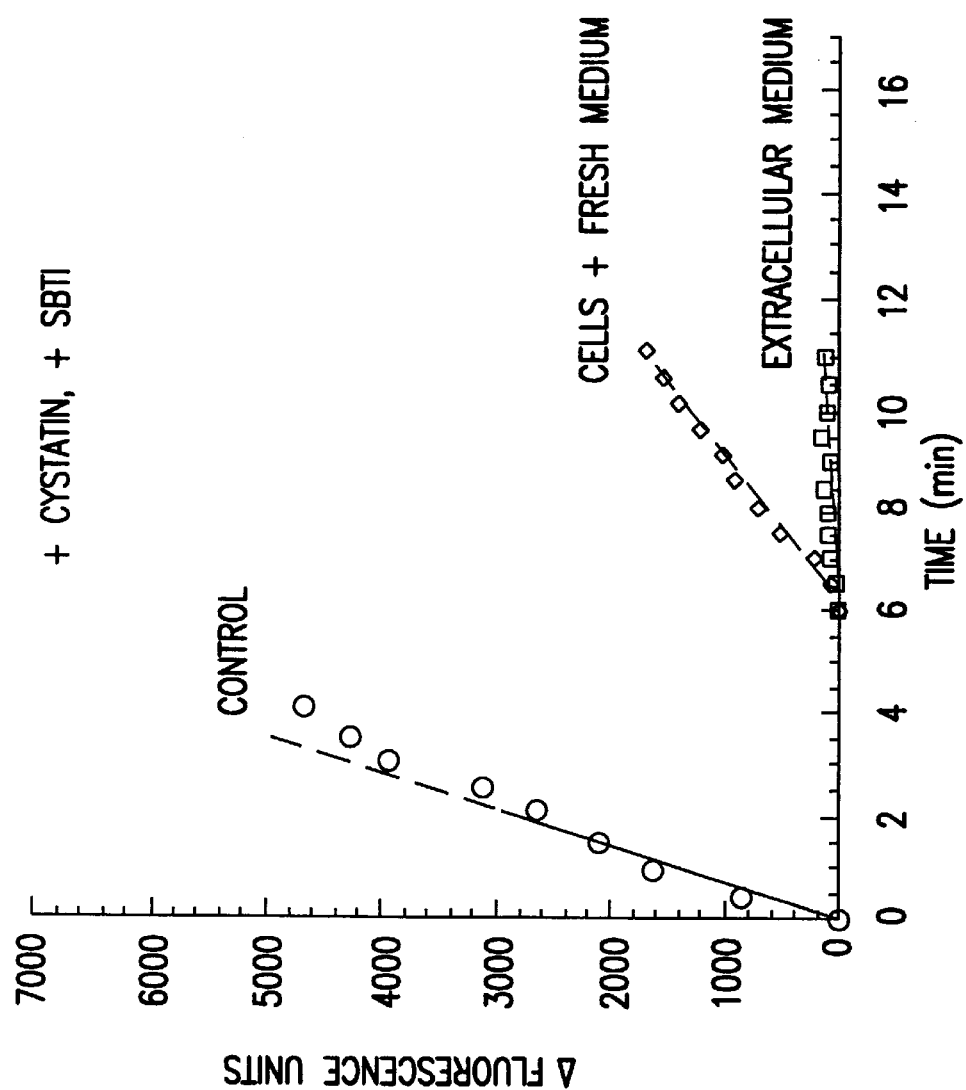

FIG. 7 shows the activity in CHO/Cat K cells and extracellular medium. Stable mock or human cathepsin K expressing cells in HBSS, pH 7.4 supplemented with 15 mM Hepes, 20 µg/ml cystatin and 100 µg/ml SBTI are incubated with 5 µM of the substrate Z-Leu-Arg-rhodamine. Substrate hydrolysis is monitored at room temperature at regular intervals. After about 3 min, the media is removed and the cells replenished with fresh substrate-free media. Substrate hydrolysis in the replenished cells and the removed media is monitored by fluorescence.

Figure 8A:
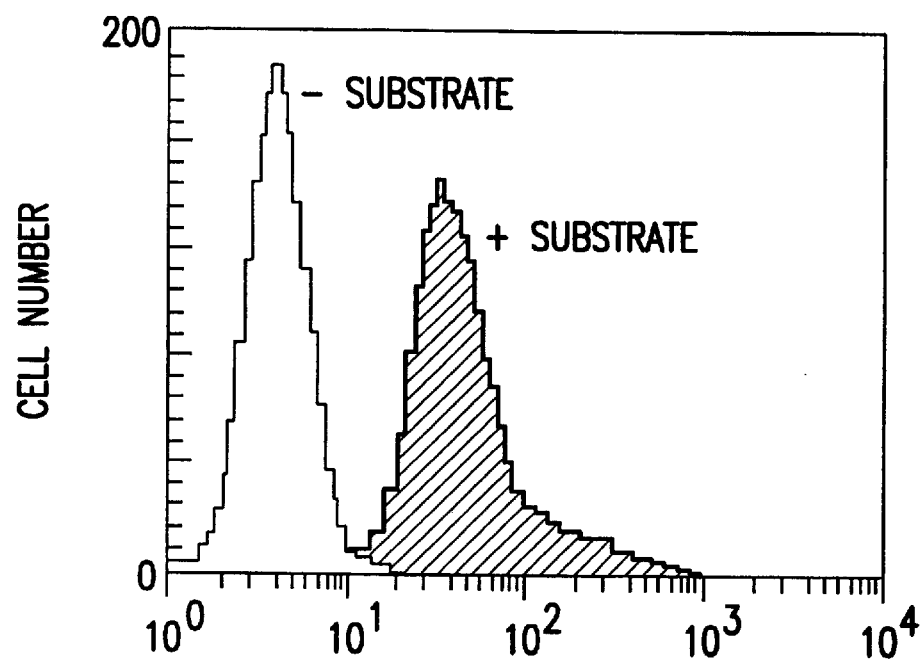
Figure 8B:
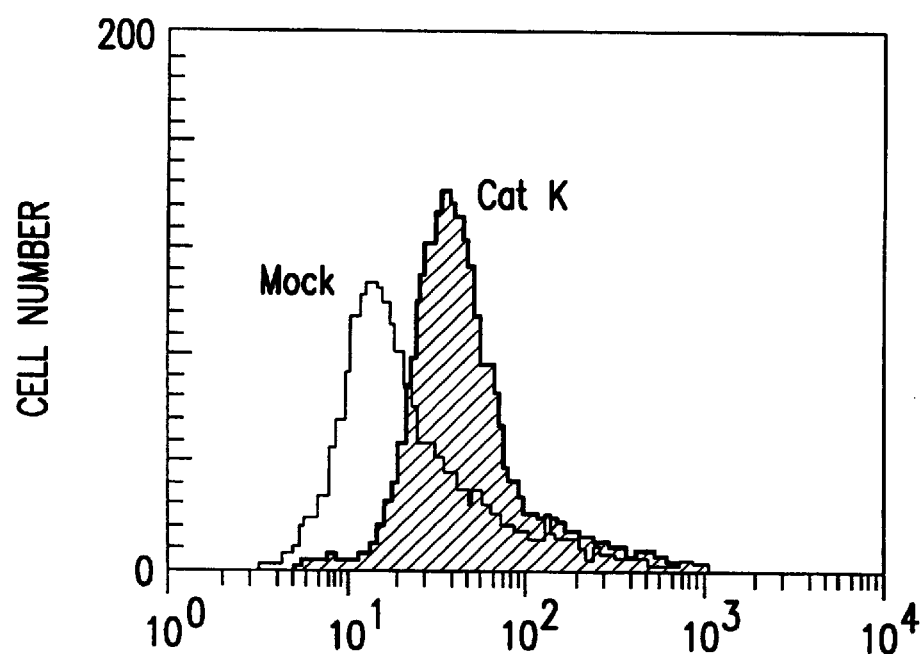
Figure 8C:
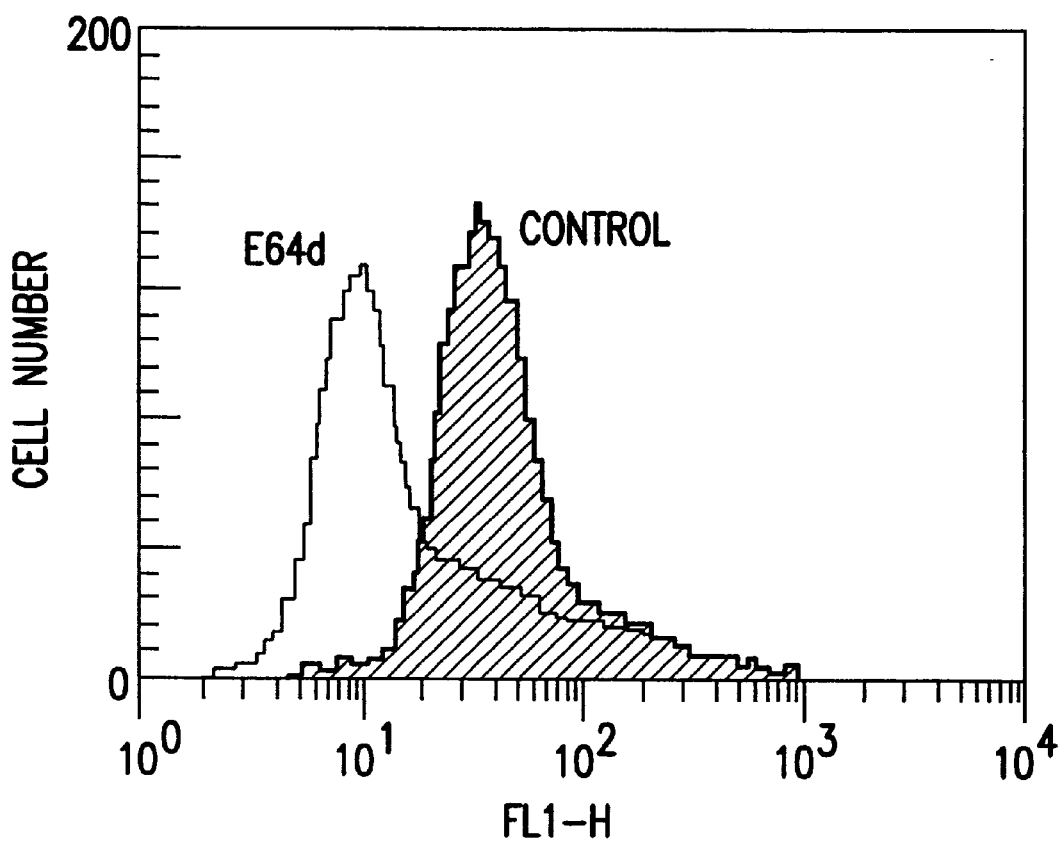

FIGS. 8A–8C show the results of the flow cytometry analysis of mock and hCat K expressing CHO cells. Pelleted cells are resuspended in $Ca^{2+}$ and $Mg^{2+}$ free PBS containing 20 µg/ml cystatin and 100 µg/ml SBTI. After a preincubation of 15 min at 3720 C., the substrate, 5 µM Z-Leu-Arg-rhodamine is added. Flow cytometry analysis is performed after a 15 min incubation at 37° C. with the substrate.

FIG. 8A shows the amount of fluorescence emitted in hCat K cells in the absence (light peak) or presence (dark peak) of the substrate.

FIG. 8B shows the amount of fluorescence emitted in mock (light peak) and hCat K (dark peak) cells in the presence of a substrate.

FIG. 8C shows the amount of fluorescence emitted in hCat K cells in the presence (light peak) or absence (dark peak) of the cell permeable cysteine protease inhibitor E64d.

DETAILED DESCRIPTION OF THE INVENTION

Definitions

Unless defined otherwise, the scientific and technological terms and nomenclature used herein have the same meaning as commonly understood by a person of ordinary skill to which this invention pertains. Generally, the procedures for cell culture, infection, transfection, molecular biology methods and the like, are common methods used in the art. Such standard techniques can be found in reference manuals such as for example Sambrook et al. (1989, Molecular Cloning —A Laboratory Manual, Cold Spring Harbor Laboratories) and Ausubel et al. (1994, Current Protocols in Molecular Biology, Wiley, N.Y.).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (Biochemistry, 1972, 11:1726–1732).

The present description refers to a number of routinely used recombinant DNA (rDNA) technology terms. Nevertheless, definitions of selected examples of such rDNA terms are provided for clarity and consistency.

The term "recombinant DNA" or "recombinant plasmid" as known in the art refers to a DNA molecule resulting from the joining of DNA segments. This is often referred to as genetic engineering.

The term "DNA segment or molecule or sequence", is used herein, to refer to molecules comprised of the deoxyribonucleotides adenine (A), guanine (G), thymine (T) and/or cytosine (C). These segments, molecules or sequences can be found in nature or synthetically derived. When read in accordance with the genetic code, these sequences can encode a linear stretch or sequence of amino acids which can be referred to as a polypeptide, protein, protein fragment and the like.

As used herein, the term "gene" is well known in the art and relates to a nucleic acid sequence defining a single protein or polypeptide. The nucleic acid can be full-length or a partial sequence encoding a polypeptide, so long as the functional activity of the polypeptide is retained.

"Restriction endonuclease or restriction enzyme" is an enzyme that has the capacity to recognize a specific base sequence (usually 4, 5 or 6 base pair in length) in a DNA molecule, and to cleave the DNA molecule at every place where this sequence appears. An example of such an enzyme is EcoRI, which recognizes the base sequence GAATTC/CTTAAG and cleaves a DNA molecule at this recognition site.

"Restriction fragments" are DNA molecules produced by the digestion of DNA with a restriction endonuclease. Any given linear genome or DNA segment can be digested by a particular restriction endonuclease into at least two discrete molecules of restriction fragments.

"Agarose gel electrophoresis" is an analytical method for fractionating double-stranded DNA molecules based on the size of the DNA. The method is based on that DNA molecules migrate through a gel as through a sieve, whereby the smallest DNA molecule has the greatest mobility and travels the farthest through the gel. The sieving characteristics of the gel retards the largest DNA molecules such that, these have the least mobility. The fractionated DNA can be visualized by staining the gel using methods well known in the art, nucleic acid hybridization or by tagging the fractionated DNA molecules with a detectable label. All these methods are well known in the art, specific methods can be found in Ausubel et al. (supra).

"Oligonucleotide or oligomer" is a molecule comprised of two or more deoxyribonucleotides or ribonucleotides, preferably more than three. The exact size of the molecule will depend on many factors, which in turn depend on the ultimate function or use of the oligonucleotide. An oligonucleotide can be derived synthetically, by cloning or by amplification.

"Sequence amplification" is a method for generating large amounts of a target sequence. In general, one or more amplification primers are annealed to a nucleic acid sequence. Using appropriate enzymes, sequences found adjacent or in between the primers are amplified. An amplification method used herein is the polymerase chain reaction (PCR).

"Amplification primer" refers to an oligonucleotide, capable of annealing to a DNA region adjacent to a target sequence and serving as the initiation primer for DNA synthesis under suitable conditions well known in the art. The synthesized primer extension product is complementary to the target sequence.

The terms "plasmid", "vector" or "DNA construct" are commonly known in the art and refer to a genetic vehicle, including but not limited to plasmid DNA, phage DNA, viral DNA and the like, which can incorporate the nucleotide sequence, or sequences of the present invention and serve as a DNA vehicle into which DNA of the present invention can be cloned. Numerous types of vectors exist and are well known in the art.

The term "expression" defines the process by which a structural gene is transcribed into mRNA (transcription), the mRNA is then translated (translation) into one polypeptide (or protein) or more.

The terminology "expression vector" defines a vector or vehicle as described above that is designed to enable the expression of an inserted sequence following transformation into a host. The cloned gene(s) (inserted sequence), usually placed under the control of control element sequences such as promoter sequences initiates the transcription of the inserted sequence. Such expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

By "eukaryotic expression system" is meant the combination of an appropriate expression vector and an eukaryotic cell line, which can be used to express a protein of interest. In some systems the gene encoding the protein may be inserted into the genome of a virus which can infect a particular host cell. Plasmid vectors containing the desired gene may also be used. In all cases, the vector will contain appropriate control elements (promoter) to express protein in the host cell. Additional components, for example a vector or viral genome coding for T7 polymerase, may also be necessary in certain expression systems. Eukaryotic cell types typically used are yeast (e.g. *Saccharomyces cerevisiae, Pischia pastoris*) transfected with a plasmid vector; insect cells (e.g. SF9, SF21) infected with baculovirus (*Autographa califomica* or *Bombyx mori*) (Luckow, Curr. Op. Biotech., 1993, 4:564–572; Griffiths and Page, 1994, Methods in Molec. biol. 75:427–440; and Merrington et al., 1997, Molec. Biotech. 8(3):283–297); mammalian cells infected with adenovirus, vaccinia virus, Sindbis virus, or semliki forest virus; and mammalian cells transfected with DNA vectors for transient or constitutive (stable) expression.

A host cell is "transfected" or "transformed" by exogenous or heterologous DNA (e.g. a DNA construct) when such DNA is introduced into the cell. These terms may be used interchangeably herein. Transfecting DNA may or may not be integrated (covalently linked) into the host cell chromosomal DNA. In prokaryotes, yeast, and mammalian cells for example, the transfecting/transforming DNA may be maintained on an episomal element such as a plasmid. With respect to eukaryotic cells, an example of a stably transfected cell is one in which the transfecting DNA has become integrated into the host cell chromosome and is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994, supra).

The nucleotide sequences and polypeptides useful to practice the invention include without being limited thereto, mutants, homologs, subtypes, alleles, and the like. It is understood that generally, the sequences of the present invention encode a functional protein. It will be clear to a person skilled in the art that the present invention comprises all variants, derivatives or fragments thereof, that express a functional protein.

As used herein, the designation "variant" denotes in the context of this invention a sequence whether a nucleic acid or amino acid, a molecule that retains a biological activity (either functional or structural) that is substantially similar to that of the original sequence. This variant or equivalent may be from the same or different species and may be a natural variant or be prepared synthetically. Such variants include amino acid sequences having substitutions, deletions, or additions of one or more amino acids, provided the biological activity of the protein is conserved. The same applies to variants of nucleic acid sequences which can have substitutions, deletions, or additions of one or more nucleotides, provided that the biological activity of the sequence is generally maintained.

The term "derivative" is intended to include any of the above described variants when comprising additional chemical moiety not normally a part of these molecules. These chemical moieties can have varying purposes including, improving a molecule's solubility, absorption, biological half life, decreasing toxicity and eliminating or decreasing undesirable side effects. Furthermore, these moieties can be used for the purpose of labeling, binding, or they may be comprised in fusion product(s). Different moieties capable of mediating the above described effects can be found in *Remington's The Science and Practice of Pharmacy* (1995). Methodologies for coupling such moieties to a molecule are well known in the art.

The term "fragment" refers to any segment of an identified DNA, RNA or amino acid sequence and/or any segment of any of the variants or derivatives described herein above.

The terms "variant", "derivative", and "fragment" of the present invention refer herein to proteins or nucleic acid molecules, which can be isolated/purified, synthesized chemically or produced through recombinant DNA technology. All these methods are well known in the art.

The term "substrate" refers to a compound that is recognized by an enzyme and is a target for its activity. Such a compound can be synthesized, isolated and purified from any chemical or biological sources including recombinant DNA technology. In the application herein the enzyme is a protease and the substrate for detecting its enzymatic activity is a peptide or a protein. Protease substrates are known to a skilled person and may be purchased from companies such as Molecular Probe (U.S.A.). In specific applications, the substrate can comprise more than one peptide molecule. Substrates are cell permeable or cell impermeable and are selected accordingly. In the present application the assay is directed to measuring the intracellular activity of an enzyme, therefore the preferred substrates are cell permeable. The substrates used herein on their own can not be detected. It is therefore necessary to couple substrates to indicator molecules thereby enabling evaluation of the enzymatic activity on the substrate. The coupling of an indicator molecule and a substrate herein is referred to as "conjugated substrate".

The structure of the cDNA encoding cathepsin K is known. WO 96113523 (supra) describes the preparation of the active form of cathepsin K. Additional publications related to the cDNA encoding cathepsin K are found in U.S. Pat. No. 5,501,969, issued to Hastings et al., Mar. 26, 1996 and PCT application WO 95/24182, published Sep. 14, 1995. Nucleotide and amino acid sequences used herein are derived from the cathepsin K sequence submitted to the Genebank having the accession number u13665.

Cell Based Assay

The present invention concerns the development of a cell-based assay for measuring the activity of cathepsin K. Particularly, the invention relates to an assay for measuring the activity of cathepsin K in an eukaryotic host cell expressing recombinant cathepsin K. More particularly the assay concerns measuring mostly intracellular recombinant cathepsin K activity.

Cathepsin K is expressed in osteoclasts and plays an important role in bone resorption. The modulation of this activity by at least one selective inhibitor may provide a useful therapeutic approach for the treatment of disorders associated with abnormal bone resorption such as for example, osteoporosis. A cell based assay measuring mostly intracellular cathepsin K activity is provided. This assay is useful in identifying cell-permeable inhibitors to cathepsin K.

The present invention provides the recombinant expression vectors and recombinant host cells useful for the purpose of present invention.

The present invention is directed to a whole cell assay for measuring the activity of recombinant cathepsin K in host cells. Briefly, an expression vector comprising the nucleotide sequence encoding cathepsin K is transfected into eukaryotic host cells, preferably mammalian host cells. The transfected cells are incubated with a cathepsin K substrate conjugated to an indicator molecule. The enzymatic activity of cathepsin K on the substrate releases the indicator molecule. The amount of the released indicator molecule is an indication of the rate of cathepsin K enzymatic activity.

Accordingly, in a first embodiment of the present invention there is provided a cell based assay for measuring intracellular cathepsin K activity in a recombinant eukaryotic cell which comprises the steps of:
 a) transforming a host cell with a vector containing a nucleotide sequence encoding a cathepsin K, to provide a transformed host cell;
 b) incubating said transformed host cell with a substrate to said cathepsin K; and
 c) determining the cathepsin K activity in said transformed host cell.

In an aspect of this invention, determination of cathepsin K activity is based on comparing the activity of cathepsin K in the transformed host cell to a standard. Non-limiting examples of standards useful for the purpose of this application include purified cathepsin K, host cells that have not been transformed and host cells transformed with a vehicle. Host cells transformed with a vehicle may include an uncloned or original vector, as in (a) or a vector cloned with any nucleotide sequence so long as cathepsin K is not expressed.

In a second embodiment of the present invention, there is provided a screening method for identifying compounds as inhibitors to cathepsin K. Particularly, the invention provides a screening method for identifying cell permeable inhibitors of cathepsin K. In this method the assay of the present invention is performed in the presence and absence of a compound and the rate of cathepsin K activity compared.

Accordingly, the invention provides a screening method for identifying a compound as an inhibitor of cathepsin K comprising the steps of:
 a) incubating an eukaryotic host cell transformed with a vector containing a nucleotide sequence encoding cathepsin K, with a substrate to said cathepsin K and in the presence of the compound;
 b) incubating an eukaryotic host cell transformed with a vector containing a nucleotide sequence encoding cathepsin K with the substrate to said cathepsin K, and in the absence of the compound; and
 c) comparing the cathepsin K activity of (a) to (b).

In an important aspect of the assay and screening method, the addition of at least one cell impermeable protease inhibitor to the whole cell assay ensures minimal interference from extracellular protease including cathepsins thereby improving the specificity of the assay and screening method for intracellular cathepsin K activity. Any cell impermeable protease inhibitor useful for the purpose of this invention is within the scope of this invention. A non-limiting example of such an inhibitor is cystatin. The concentration of cystatin used is dependent on reaction conditions of the assay which include type of host cell, cell number, culture media, cell growth, etc.. Therefore the concentration of cystatin to be added to the reaction assay is about 0.1 to 100 $\mu$g/ml, preferably about 1 to 80 $\mu$g/ml, more preferably about 5 to 50 $\mu$g/ml and most preferably about 10 to 30 $\mu$g/ml.

In an aspect of this invention, the substrates useful for the assay and screening method comprise di- and tri-peptides. These are known in the art, some non-limiting examples can be found in U.S. Pat. No. 5,871,946, others are available commercially from companies such as Molecular Probes (U.S.A.). In a specific aspect, the substrates are cell permeable and are particularly useful for detecting recombinant cathepsin K activity within the host cell. In a more specific aspect, the substrate comprises one or more of the di-peptide, Z-Leu-Arg.

In a further aspect of this invention, the substrates are conjugated to an indicator compound having two forms, the first when conjugated and second when non-conjugated. "Conjugation" herein refers to a means for attaching an indicator compound to a substrate. As a consequence of enzymatic activity on the first form, the conjugated substrate, the indicator compound or a component thereof is released. In the second form the released indicator compound or a component thereof is detectable, therefore a measure of the indicator compound present in the second form is a measure of enzymatic activity on the conjugated substrate. Indicator compounds are known in the art, some non-limiting examples can be found in U.S. Pat. No. 5,871,946, others are available commercially from companies such as Molecular Probes (U.S.A.). Indicator compounds useful for the purpose of the present application include fluorophores such as rhodamine and aminomethylcoumarin, and chromophores such as para-nitroaniline. Additionally, substrates can be labeled by means including radioactivity and fluorescence.

The indicator compounds in the second form can be detected by appropriate means, which correspond to the specific indicator compound. All conventional detection means useful for the purpose of this invention are within the scope of this application. Non-limiting examples include fluorescent light emission, phosphoimaging and spectrophotometrically for fluorophores, radioactive labeled compounds and light emitting compounds, respectively.

In a preferred aspect the substrates are conjugated to fluorophores, such as rhodamine and aminomethylcoumarin and detected by fluorescent light emission.

In a most preferred aspect, the conjugated substrate is selected from Z-Leu-Arg-AMC and [Z-Leu-Arg]$_2$-rhodamine.

The conditions under which the cell-based screening methods and assays of the present invention are practiced are well known in the art: i.e., physiological pH; salt conditions such as those represented by such commonly used buffers such as PBS or in tissue culture media; a temperature of about 18° C. to about 42° C., etc.

The above-described screening methods are explicitly directed to testing "a" compound, it will be clear to a person skilled in the art that such a method can be adapted to testing multiple compounds, e.g., combinatorial libraries to determine if any member of such a collection is inhibitory to cathepsin K activity. Accordingly, the use of collections of compounds, or individual members of such collections is within the scope of this invention.

The recombinant vectors and host cells described and used in the methods and assays are all within the scope of the present invention.

Accordingly, the present invention provides recombinant eukaryotic expression vectors comprising the nucleotide sequence encoding the pre-pro cathepsin K. A variety of eukaryotic expression vectors can be cloned to express recombinant cathepsin K in host cells. In a preferable aspect the vector is a mammalian expression vector. Commercially available mammalian expression vectors that are useful for the present invention include but are not limited to, pMClneo (Stratagene), pSG5 (Stratagene), pcDNAI and pcDNAIamp, pcDNA3, pcDNA3.1, pcr3.1 (Invitrogen), EBO-pSV2-neo (ATCC 37593), pBPV-1(8-2) (ATCC 37110), pdBPV-MMTneo(342-12) (ATCC 37224), pRSVgpt (ATCC 37199), pRSV neo (ATCC 37198), pSV2-dhfr (ATCC 37146), and the PT7TS oocyte expression vector (or any similar expression vectors containing the globin 5' UTR and the globin 3' UTR). The choice of the vector will depend upon the host cell type used, level of expression and the like.

The present invention further provides eukaryotic host cells engineered to contain and/or express the recombinant expression vector comprising the nucleotide sequence encoding pre-pro cathepsin K. The eukaryotic host cells include insect cells such as SF9 and SF21, and mammalian cells that can be derived from species including but are not limited to human, bovine, porcine, monkey and rodent. Non-limiting examples of commercially available mammalian cells suitable for the expression of recombinant cathepsin K include CHO K1, COS-7, NIH 3t3, MDCK, OK, HEK-293 and U937.

In selecting a host cell, it is important to evaluate background or endogenous protease activity in host cells using similar conditions as the present invention. Ideally endogenous protease activity in the host cell is low or absent allowing recombinant cathepsin K activity in the recombinant host cell to be determined.

In an aspect of the present invention, the host cell is a mammalian host cell. Preferably, the mammalian host cell having low or no endogenous cathepsin K activity. More preferably, the recombinant host cell having low or no endogenous cathepsin K activity is also capable of processing the recombinant pre-pro-cathepsin K to the mature and active cathepsin K. Additionally, the mammalian host cells are either transiently or stably transfected. In a specific aspect, the host cell is stably transfected and a stable cell line expressing recombinant cathepsin K is established.

Therefore in a preferred aspect, the mammalian cell line with low or no endogenous cathepsin K activity is stably transfected with a recombinant vector comprising the nucleotide sequence encoding the pre-pro cathepsin K and is capable of processing the pre-pro-cathepsin K to the mature and active cathepsin K enzyme. The mammalian cell line CHO-K1 is exemplary and is used herein to demonstrate the application of the present invention.

The expression of the pre-pro-mature enzyme and its activation to the mature enzyme (50%) within the cell is consistent with the autoactivation of cathepsin K. Purified pro-cathepsin K can be activated to the mature form by lowering the pH to 4.0 (Teitelbaum, S. L., et al., 1997, *J Leukoc Biol* 61:381–388). This decrease in pH is believed to cause a change in the conformation of the protein allowing the active site cysteine to autocatalyze to the active mature form of the enzyme.

Using a CHO expression system and immunofluorescence staining, cathepsin K shows host cell localization consistent with the lysosomal compartment. Since lysosomes can have pH values of about 4–5, cathepsin K is believed to be autocatalytically activated within the lysosomes. Further, secreted cathepsin K is detected in the CHO culture media, consistent with reports that cysteine proteases of the papain family are secreted (Berti, P. J., and Storer, A. C., 1995, *J Mol Biol* 246:273–83). It is interesting that the secreted form of the enzyme has a molecular weight consistent with the pro-mature cathepsin K and does not appear to be processed. This may be due to several factors such as, the culture media where the cells are growing has a neutral pH environment and this may not be conducive to activating to the mature form. The mature form of cathepsin K detected in the CHO cells is retained within the cells.

In an environment of bone resorption, cathepsin K may be secreted as the pro-mature form but then has to be activated to the mature form in the milieu surrounding the osteoclasts. Resorption lacunae, having an acidic microenvironment formed by osteoclasts, may provide the conditions for autocatalytic activation of cathepsin K.

Cathepsin L and S are the closest homologues of cathepsin K with amino acid sequence identities of 51 and 56%, respectively. Cathepsin K also has a very similar $S_2S_1$ substrate specificity to cathepsin S, which could cause difficulties in establishing a recombinant cell based assay specific for cathepsin K. The increased activity measured by peptide substrates hydrolysis in the transfected hCat K compared to mock cells, demonstrates that recombinant cathepsin K activity is expressed at a detectable level above endogenous proteases. Cathepsin B is a ubiquitously expressed protease and was detected in the CHO cells. This is not a problem in the development of the present assay since the Cat B substrate, Z-Arg-Arg-AMC (Rifkin, B., et al., 1991, *Biochem Biophys Res Commun* 179:63–69), is not efficiently utilized by the CHO cells. Two other peptide substrates that are not valid substrates for cathepsin K, L, S or B, Z-Phe-Ala-AMC and Z-Phe-Gly-AMC, served as negative controls in assaying cellular extracts.

A significant amount of extracellular proteolytic activity is detectable in this assay this activity is mostly inhibited by cystatin. Several approaches are used to ascertain that the amount of substrate hydrolysis in the hCat K transfected stable cell line is mostly due to intracellular cathepsin K activity. Firstly, there is no detectable cathepsin K activity in the extracellular media removed from cells after initiating the reaction with Z-Leu-Arg-Rho in the presence of cell impermeable inhibitors cystatin and SBTI. However there is a demonstrable increase in fluorescence in the remaining cells, indicating that indeed the cells are mostly responsible for the proteolytic activity and that the selected substrate is cell permeable. Secondly, FACS experiments demonstrate that hCat K cells have an increase in fluorescence when compared to mock cells in the presence of the substrate Z-Leu-Arg-Rho, this increase in fluorescence is inhibited with the addition of E64d. These exhaustive methods validate the specificity of the assay of the present invention for intracellular cathepsin K.

Recently, a mouse knockout of cathepsin K characterized by an increase in trabecular bone and an overall decrease in bone resorption has been developed (Saftig, P., et al., 1998, *Proc Natl Acad Sci U S A* 95(23):13453–13458). This knockout is similar to the human gene mutation linked to pycnodysostosis confirming and reinforcing the relevance of cathepsin K in pathophysiological conditions, such as osteoporosis.

Considering the limited availability of osteoclasts and lack of established osteoclast cell lines the development of a cell based assay for identifying inhibitors of cathepsin K is very important. This assay provides a useful tool for the rapid analysis and screening of cell permeable cathepsin K inhibitors. Cell permeable cathepsin K inhibitors identified by use of this assay would be useful in obtaining potential therapeutic agents in the treatment of individuals in need of such treatment. An example of such an individual is a person with osteoporosis or any bone resorption related disorders.

The following non-limiting examples are presented to better illustrate the invention and are not meant to limit the scope of the invention.

EXAMPLES

Materials

Oligonucleotide primers are synthesized at Research Genetics (Al, USA). Prestained molecular weight markers are purchased from Life Technologies (NY, USA). Fluorogenic peptides are purchased from Bachem (Switzerland), Molecular Probes (OR, USA) or Novabiochem (CA, USA). The [Z-Leu-Arg]$_2$-rhodamine substrate is custom synthesized at Anaspec (CA, USA). Cysteine protease inhibitors E64, E64c and E64d are purchased from Sigma (ON, Canada).

Example 1

Cloning and Sequencing of the Cathepsin K cDNA

The full-length cDNA of human cathepsin K (Shi, G. P., et al., 1995, FEBS *Lett* 357:129–34; Bromme, D., and Okamoto, K., 1995, *Biol Chem Hoppe Seyler* 376:379–84) is PCR amplified from a commercially available human bone marrow cDNA library (Clontech, CA, USA) using the following primer pair: forward primer ACAGATTTCCAT-CAGCAG (SEQ ID NO. 1) and reverse AGTAGGAAG-GATCATTTG (SEQ ID NO. 2). The reaction is performed in a GeneAmp 2400 PCR system from Perkin-Elmer for 30 cycles of denaturation (94° C., 30 s), annealing (55° C., 30 s) and extension (72° C., 1 min) using the Expand High Fidelity PCR System (Boehringer Mannheim, PQ, Canada). The primary amplification product is used as a template in a second round of PCR under the same amplification conditions, using specific nested primers containing EcoRI and NotI restriction sites: GAAGCCAGACGAATTCACA-GATTTCCATCAGCAG (SEQ ID NO. 3) and ATTAGTCT-TGCGGCCGCGGATCCTCACATCTTGGG-GAAGCTGGCCAGGTT (SEQ ID NO. 4). The product of the second round of PCR is digested with EcoRI-NotI (obtained from Boehringer Mannheim, PQ, Canada) and ligated into an EcoRI-NotI pcDNA3.1 vector (Invitrogen, CA, USA). Sequence analysis is performed on an ABI 373A DNA sequencer (Applied Biosystems, CA, USA) using the Dye Deoxy Terminator Kit (Applied Biosystems, CA, USA), confirming that the amplified and cloned DNA comprises the full length cDNA encoding the signal sequence, pro-domain and mature enzyme of human cathepsin K. Further the cloned cDNA is identical to the published sequence (Bromme, D., and Okamoto, K., 1995, *Biol Chem Hoppe Seyler* 376:379–384). The recombinant vector is referred to hereinbelow as pcDNA3.1/hCat K.

Example 2

Construction of a Cathepsin K Stable Cell Line

The vectors pcDNA3.1 and pcDNA3.1/hCat K are transfected into Chinese hamster ovary cells (CHO-K1; American Type and Culture Collection CCL-61) using liposome-mediated transfection with the Lipofectamine reagent (Life Technologies, NY, USA) as described in the supplier's instructions. Using methods well known in the art, stable transfectants are clonally selected. In a non-limiting example, the cells are grown in a monolayer in HyQ-CCM5 medium (Hyclone, UT, USA) supplemented with 2% heat-inactivated FBS, 100 µg/ml streptomycin, 100 units/ml penicillin, 100 µg/ml gentamicin and selected in 500 µg/ml G418 (Life Technologies, NY, USA). Cells stably transfected with pcDNA3.1 (mock cells) are identified by southern blot analysis (data not shown). Cells stably transfected with pcDNA3.1/hCat K (hCat K cells) are identified by western blot analysis.

Mock and hCat K stable transfectants are selected with the neomycin analogue (G418) for one month by limited dilution cloning. Mock (control) and hCAt K selected stable tranfectants are used in the subsequent determination of cathepsin K expression and activity, and the substantiation of the present assay.

Example 3

Immunoblot Analysis

Cultured tranfectants are pelleted, resuspended in PBS and sonicated for 3×10 s using a Kontes Ultrasonic Disrupter. The cell suspension is centrifuged at 1,000×g for 10 min at 4° C. and the resulting cellular extract supernatants used to determine cathepsin K expression and activity. Protein concentrations are determined on all the supernatants using the Pierce Coomassie Protein Reagent (Pierce, Ill. USA) as described in the manufacturer's instruction.

For immunoblot analysis, cellular extracts are prepared as described above with the exception that PBS is supplemented with the Complete Protease Inhibitor Cocktail (Boehringer Mannheim, PQ, Canada) at two fold the suggested concentration in the manufacturer's instructions.

In order to evaluate the amount of cathepsin K secreted by the transfectants, the cells are grown for 24 h in serum free media and the media collected. The serum-free cell culture media in which the transfectants are grown are concentrated using Centriplus-10 concentrators (Amicon, MA, USA) according to the manufacturer's instruction and total protein determined.

SDS-PAGE is a method well known in the art. Briefly, 3μg of total cell protein are resolved on precast 4–20% tris-glycine acrylamide gels (Novex, CA, USA) and electrophoretically transferred to PVDF membranes using a Novex immunoblot transfer apparatus, according to manufacturer's instructions. Nonspecific sites are blocked with 5% non-fat dry milk in PBST (PBS, 0.05% Tween) for 1 h at room temperature, and the blotted membranes washed twice for 5 min/wash in PBST. The blocked blots are probed with a 1/20,000 dilution in 1% BSA/PBST of an anti-human Cat K rabbit polyclonal antibody (AxyS Pharmaceuticals, CA, USA) for 1h then washed four times for 15 min/wash in PBST. The blots are then probed with a 1/3,000 dilution in 1% BSA/PBST of a horseradish peroxidase-linked anti-rabbit IgG antibody (Amersham, ON, Canada) for 1 h, then washed 4 times in PBST. Immunoblot analysis is performed using the Renaissance Western Blot Chemiluminescence Reagent (NEN, MA, USA) according to manufacturer's instruction.

Figure 1:
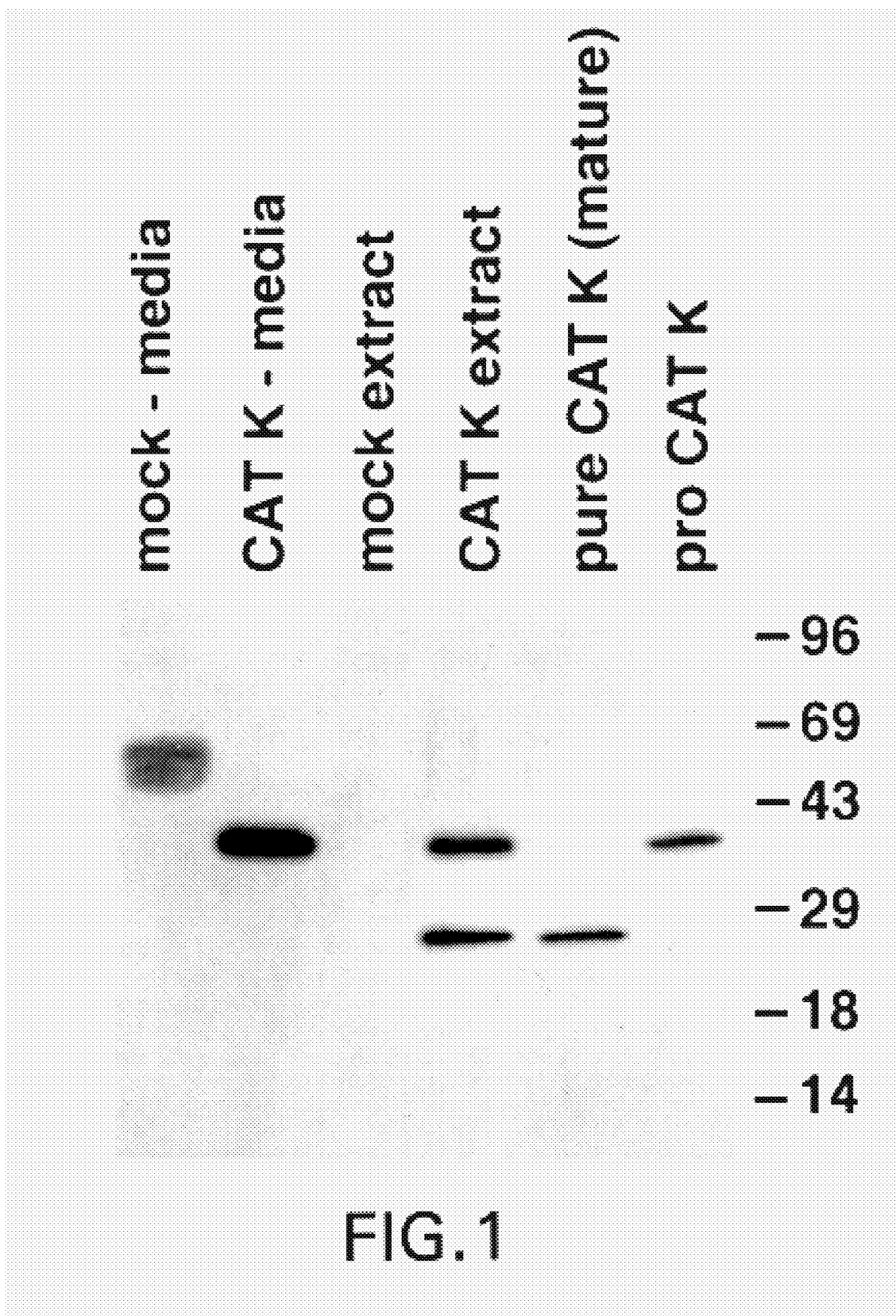
FIG. 1 shows the results of a Western blot analysis of cathepsin K in cells transformed with pcDNA3.1 (mock) and pcDNA3.1/hCat K (cathepsin K) expressing CHO cells. Supernatant of cell extracts are prepared by resuspending pelleted cells in PBS, then sonicating and collecting the supernatant by centrifuging the disrupted cells at 1,000×g for 10 min. Serum-free media in which mock and cathepsin K expressing cells are grown, are collected and concentrated. Protein concentrations are determined and 3 µg of total cell protein of the supernatants and the concentrated media are separated by electrophoresis, transferred to a polyvinylidene difluoride (PVDF) membrane, and probed with a human cathepsin K specific antiserum. Standards (10 ng) of human mature cathepsin K (pure Cat k mature) and pro-mature (pro Cat K) are shown. Molecular weight markers are as designated. The results show a non specific reactive band in the mock media that is absent in the mock cell extract. The Cat K media show a band with an apparent molecular weight equivalent to the pro-mature cathepsin K and the Cat K extract shows two bands with apparent molecular weights equivalent to the pro-mature and mature forms of the enzyme. The presence of the mature form in the Cat K extracts indicates the intracellular processing of the pro-mature enzyme.

FIG. 1 shows the presence of extracellular and intracellular cathepsin K (Cat K) expression by immunoblot analysis. The media of the mock cells appears to have a cross reacting artifact band which does not correlate with any relevant molecular mass for cathepsin K. Mock cells supernatant does not appear to be reactive with the cathepsin K antisera. The media of the hCat K cells have an immunoreactive band of 37 kDa, this co-migrates with pro-cathepsin K. hCat K cells supernatant have two immunoreactive bands, 27 and 37 kDa, these co-migrate with the mature and pro-cathepsin K, respectively. The results of the western blot demonstrate that intracellular activation of pro-cathepsin K to the mature form occurs in the transfected CHO cells and appears to constitute approximately 50% of expressed cathepsin K enzyme. About 40% of total cathepsin K expressed by CHO cells is secreted into the media.

This intracellular activation of cathepsin K to the mature form is not restricted to CHO cells. Transient transfection in COS-7 cells results in a similar ratio of mature to pro-cathepsin K (data not shown).

Therefore, the present invention encompasses all mammalian cells that are either transiently or stably transfected with a vector containing a nucleotide sequence encoding cathepsin K.

Example 4
Immunofluorescence Localization of Cathepsins

Stably transfected mock or hCat K cell lines are trypsinized and seeded at 500,000 cells/well in sterile 35-mm tissue culture dishes containing sterile coverslips. After an overnight incubation at 37° C., cells are washed in PBS, immersed in a fresh methanol: 1% formaldehyde solution and incubated for 15 min at −20° C. followed by 10 min at room temperature. Cells are washed again with PBS and briefly placed in PBS containing 50 mM NH$_4$Cl and rinsed in PBS followed by a 20 min incubation in 2% BSA and 0.2% gelatin in PBS, and final washes with PBS. The cells are probed with a 1/1,000 dilution of one of the following primary antibodies, anti-human Cat K mouse monoclonal antibody (Medicorp, PQ, Canada), or anti-human cathepsin B sheep polyclonal antibody (Serotec, NC, USA). A 90 min incubation with the primary antibody is followed by a wash in PBS and a 45 min incubation with a 1/200 dilution of the following respective FITC-conjugated secondary antibodies: donkey anti-mouse IgG (Amersham, ON, Canada), or donkey anti-sheep IgG (Molecular Probes, OR, USA). In a final step the cells are washed in PBS and the coverslips inverted on a slide containing a drop of the Prolong Anti-fade Kit (Molecular Probes, OR, USA). Slides are examined using a Zeiss Axiophot fluorescence microscope. Exposures are manually adjusted to the automatic setting obtained with the CHO/hCat K cells incubated with the anti-hCat K primary antibody. For CHO/mock cells incubated with the primary antibody anti-cathepsin K, exposure is increased to better visualize cellular background level fluorescence.

Figure 2A:
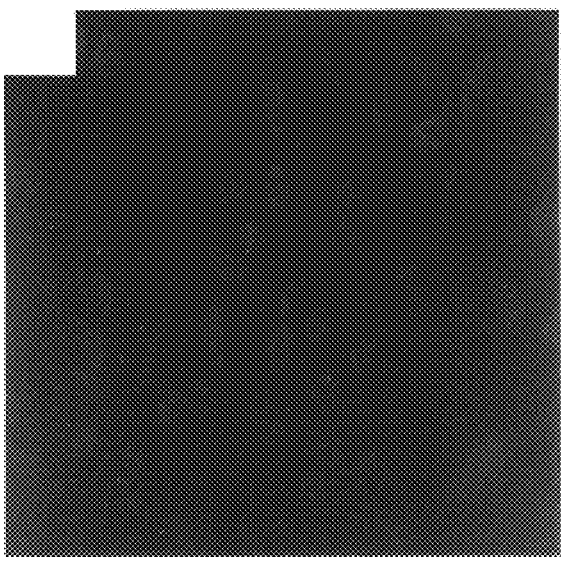
FIGS. 2A–2C show the immunofluorescence localization of cathepsin K and B in mock and cathepsin K expressing CHO cells. The cells are fixed and permeabilized in a fresh methanol/1% formaldehyde solution for 15 min at −20° C., stained with a primary antisera and corresponding FITC-conjugated secondary antibody.
Figure 2B:
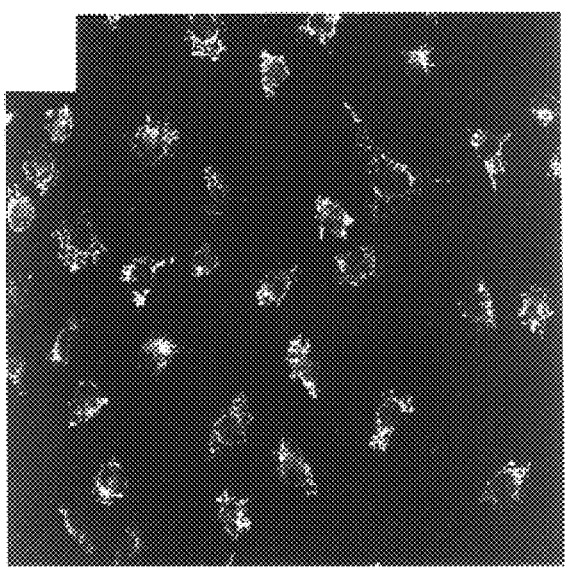
Figure 2C:
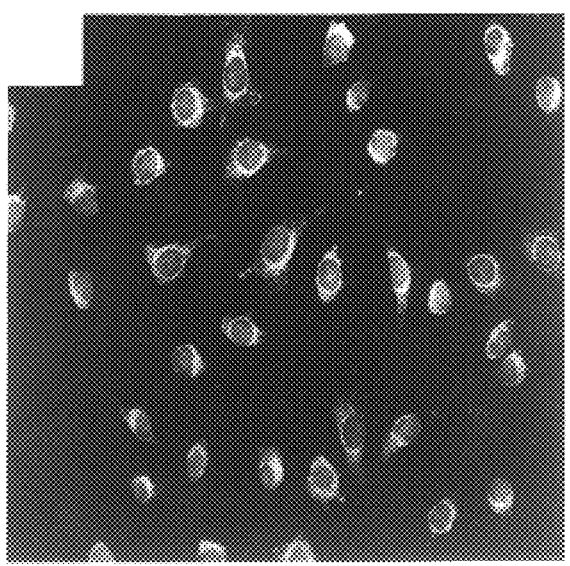

The localization and distribution of expressed cathepsin B and K is shown in FIG. 2. The panels show the immunofluorescence analysis of mock and hCat K cells probed with antisera to cathepsin B and K. In FIG. 2A, cathepsin K antisera detected a faint signal of fluorescence in mock cells suggesting little or no endogenous cathepsin K is present in CHO cells. This is consistent with immunoblot of FIG. 1, in which cathepsin K protein in mock cells was not detected. In FIG. 2C, mock cells probed with cathepsin B antisera resulted in diffused cytoplasmic staining with some rimming around the nucleus. In FIG. 2B hCat K cells probed with cathepsin K antisera resulted in an intense punctate staining throughout the cytoplasm. This intense punctate signal for cathepsin K is consistent with a distribution of the immunoreactive protein in the lysosomal compartment. Localization of cathepsin K to the lysosomal compartment within osteoclasts has been previously reported (11).

Example 5
Enzyme Assays in Cellular Extracts

Cathepsin K is a cysteine protease with a substrate $S_2P_2$ specificity of a positively charged residue such as arginine in the P1 position and a large hydrophobic residue in the P2 position. The utilization of various di- and tri-peptide substrates by the recombinant cathepsin K is evaluated. For the purpose of this invention various cell permeable di- and tri-peptides compounds described in the literature can be used as substrates to cathepsin K (for example 13 and U.S. Pat. No. 5,871,946). These are conjugated to indicator compounds. Indicator compounds include commercially available compounds from companies such as for example Molecular Probes (USA) and those described in U.S. Pat. No. 5,872,946.

The indicator compounds used herein are fluorophores. These are compounds having two states, a first being non-fluorogenic when joined to a peptidic substrate and a second being fluorogenic when the peptidic substrate is enzymatically cleaved off leaving the indicator compound. Non-limiting examples of fluorophore indicator compounds useful for the present invention are aminomethylcoumarin (AMC) and rhodamine 110. These fluorophores were conjugated to the P' position of the peptide substrates. Rhodamine conjugated substrates were tested along with AMC conjugated substrate, since rhodamine dipeptides are believed to be more cell permeable.

The enzymatic activity of purified cathepsin K (3 nM) and transfectants' supernatants (5 μg/ml of protein) is determined by following the rate of hydrolysis of different peptide substrates conjugated to either AMC or rhodamine. Assays are performed at room temperature in 200 μl of buffer A [50 mM MES (2-(N-morpholino)ethanesulfonic acid) buffer, pH 5.5, containing 2.5 mM EDTA, 2.5 mM dithiothreitol, 10% DMSO]. Substrate hydrolysis is monitored over a period of 10 min at room temperature in a Cytofluor 4000 fluorescent plate reader (Perseptive Biosystems, MA, USA). Cathepsin K activity measurements are calculated as initial rates over the first 5 min of the reaction.

FIG. 3 shows the rate of hydrolysis of various substrates by the supernatants of mock and hCat K cells. The data shows that Z-Leu-Arg (Z=benzyloxycarbonyl) conjugated to either AMC or rhodamine provides the largest measurable activity among the tested substrates. The rate of hydrolysis using the Z-Leu-Arg substrates in the hCat K cells extract is at least 12 fold greater than the mock cells extract, this demonstrates that the expressed cathepsin K has significant activity above endogenous proteases in the transfected cells. The use of Z-Phe-Arg substrates resulted in 1.8–3 fold lower activity when compared to the corresponding Z-Leu-Arg substrates.

The most selective cathepsin K substrate, Z-Pro-Arg (M.D. Percival, personal communication) gave no detectable activity in mock cells extract with AMC or rhodamine conjugated substrates. However, since the level of detectable activity in hCat K cells extract is too low, this substrate does not appear to provide sufficient sensitivity for the development of a cell based assay.

The amount of immunoreactive cathepsin K in cell extracts is quantified by comparison to the immunoreactivity of purified cathepsin K standard, and the mature CHO cathepsin K is estimated to have 15% of the activity of the purified enzyme when using the Z-Leu-Arg-AMC substrate.

Example 6

The Effect of Cystatin on Cathepsin Activity

The effect of cystatin on expressed recombinant cathepsin K and purified cathepsin K is evaluated. Cystatins are a family of endogenous protein inhibitors of cathepsins. FIG. 4 shows % inhibition of different concentrations of cystatin on the rate of hydrolysis of the Z-Leu-Arg-rhodamine substrate by purified cathepsin K and hCat K extract, the graph shows that the $IC_{50}$ of cystatin is 200 ng/ml and 90 ng/ml, respectively. This result demonstrates that the activity of the recombinant cathepsin K expressed by the CHO tranfectants can be inhibited in a similar fashion as purified cathepsin K.

Example 7

Selection of Inhibitors to Extracellular Proteases

Proteases including cathepsins are secreted and active extracellularly, therefore in order to develop a cell based assay that measures mostly intracellular recombinant cathepsin K activity it is important to select cysteine protease inhibitors that affect mostly extracellular cathepsins. To that end different protease inhibitors are evaluated with the purpose of minimizing interference by extracellular proteases including secreted cathepsin K.

To determine the effect of different inhibitors on cathepsin K activity, mock and hCat K whole cells are preincubated with 1 $\mu$l of vehicle (control) or an inhibitor for 15 min at room temperature followed by the addition of the substrate. All inhibitors are prepared as stock solutions in DMSO (dimethylsulfoxide) and assays performed with a final DMSO concentration of 1.5%.

Mock and hCat K cells are plated into 96 well tissue culture plates as described in materials and methods and the activity is determined using the Z-Leu-Arg-rhodamine substrate. The assay is performed in a final volume of 200 $\mu$l, in the presence of one of the following inhibitors: EDTA (1 mM) a metalloprotease inhibitor; soybean trypsin inhibitor (SBTI, 100 $\mu$g/m); a trypsin inhibitor; pepstatin A (0.7 $\mu$g/ml); an aspartyl protease inhibitor; and cystatin (20 $\mu$g/ml), a cysteine protease inhibitor. The concentration of cystatin used to inhibit extracellular cysteine protease activity in the present Example is based on the results obtained in Example 6, in which the effect of cystatin on the activity of both pure cathepsin K and hCat K cell extracts is examined.

The results shown in FIG. 5 demonstrate that only in the presence of cystatin there is a decrease in protease activity in the whole hCat K cells, the other protease inhibitors appeared to have little effect. This result is consistent with the presence of active cysteine protease in the extracellular medium most probably secreted active cathepsin K. Cystatin is a 12 kDa reversible inhibitor of cysteine proteases of the cathepsin family, which does not permeate into cells (cell permeability tested in CACO-2 cells, J. Guay and J. Mancini, unpublished results). Therefore, addition of cystatin to whole cell assay for cathepsin would ascertain that hydrolysis of the substrate is mostly due to intracellular cathepsin K and not to extracellular protease activity.

Mock cells (FIG. 5) contain no measurable activity in the absence or presence of any of the protease inhibitors. One plausible explanation for the increased extracellular activity in the cathepsin K expressing cells compared to the mock cells is that the overexpressed cathepsin K may be activated or activate several other secreted cysteine proteases.

In subsequent experiments, cystatin and SBTI are utilized in all whole cell assays. SBTI is added to counteract the possible effect of trypsin used in the subculturing of the transformed host cells.

Example 8A

Enzyme Assays in Whole Cells

Unless otherwise indicated, cathepsin K activity in intact cells is conducted by challenging the cells with 5 $\mu$M of the substrate [Z-Leu-Arg]$_2$-rhodamine in the presence of cystatin and SBTI. Using sterile 96-wells culture plates (Nunc, DK, Denmark), 50,000 mock or Cat K expressing stable cell lines are dispensed into each well and incubated for 24 h. Using the Skanwasher 300 plate washer (Skatron, VA, USA) the cells are washed twice with PBS containing $Ca^{2+}$ and $Mg^{2+}$. Then, pre-incubated for 15 min at room temperature in 200 $\mu$l HBSS (Hank's buffered saline solution), pH 7.4, supplemented with 15 mM Hepes, 20 $\mu$g/ml cystatin (Calbiochem, CA, USA) and 100 $\mu$g/ml soybean trypsin inhibitor (Sigma, ON, Canada). The pre-incubated cells are then challenged with the addition of 2 $\mu$l of [Z-Leu-Arg]$_2$-rhodamine (500 $\mu$M stock solution in DMSO to a final 5 $\mu$M concentration). Substrate hydrolysis is monitored at room temperature in a Cytofluor 4000 fluorescent plate reader (Perseptive Biosystems, MA, USA).

Example 8B

Evaluation of Substrates for Optimal Intracellular Cathepsin K Activity

In Example 5 and FIG. 3 the use of di-peptide substrates are evaluated for the purpose of optimizing the measurement for cathepsin K activity in cell extracts. In the process of selecting the optimal substrate for a whole cell assay, di- and tri-peptide substrates are examined. The assays are performed in the presence of cystatin and SBTI. FIG. 6 shows that the results obtained for whole cell assay are comparable to those obtained for cell extracts. That is, the substrate peptide Z-Leu-Arg conjugated with AMC or rhodamine is suitable for measuring intracellular cathepsin K activity.

However, the substrates Z-Pro-Arg-Rho, Z-Phe-Arg-Rho, and Z-Leu-Arg-Rho are not good substrates in cell extracts (FIG. 3) but very good in the whole cell assay. The Z-Leu-Arg peptide conjugated to rhodamine is the best peptide substrate in the cell extracts. A possible explanation is that the measurement of intracellular activity is dependent not only on the rate of substrate hydrolysis but also on its ability to enter the cell.

Example 9
Substrate Hydrolysis Attributed to Intracellular Cathepsin K Activity Extracellular proteases account for 90% of the measurable protease activity in cell based assays with the dipeptide substrate Z-Leu-Arg-Rho (FIG. 5). This can be attenuated with cystatin but the question still arises whether the residual activity in the presence of cystatin is truly intracellular or is due to an incomplete inhibition of extracellular activity by cystatin. Several approaches are investigated to address this question.

The first approach is based on removing the substrate from the extracellular environment. Briefly, cells are challenged with the substrate, Z-Leu-Arg-Rho for 3 minutes then the media containing the substrate is removed and the cells washed, and fresh media without substrate added. The rate of substrate hydrolysis is followed in the cells and the removed media by fluorescence monitoring. As shown in FIG. 7, the cells in the fresh media demonstrate a continued increase in fluorescence while the removed media does not. This result demonstrates that the increase in fluoresence is due to cleavage of the initially added substrate by intracellular cathepsin K hydrolysis rather than extracellular proteases.

TABLE 1

| Inhibitor | IC50 (nM) | |
|---|---|---|
| | Pure Cat K | Whole cell |
| E64 | 30 | 576 |
| E64c | 41 | 307 |

Table 1 shows the effect of the inhibitors E64 and E64c. Stable mock or hCat K expressing cells are resuspended in HBSS, pH 7.4 supplemented with 15 mM Hepes, 20 µg/ml cystatin and 100 µg/ml SBTI. Pure cathepsin K enzyme is resuspended in buffer A. Enzyme suspensions are preincubated with the designated inhibitor for 15 min before initiating the reaction with 5 µM of the substrate Z-Leu-Arg-Rhodamine.

EXAMPLE 10
Flow Cytometry Analysis

In a third and final approach to validate the cell based assay for cathepsin K, fluorescence assisted cell sorter (FACS) analysis is used.

Stable mock or hCat K cell lines are trypsinized and resuspended at a density of 1 million cells/ml in $Ca^{2+}$ and $Mg^{2+}$ free PBS, 20 µg/ml cystatin and 100 µg/ml soybean trypsin inhibitor. Cells are preincubated for 15 min at 37° C. in the presence of vehicle or an inhibitor followed by the addition of the substrate, [Z-Leu-Arg]$_2$-rhodamine (5 µM). Flow cytometry analysis is performed using a FACSCalibur system (Becton Dickinson, CA, USA) equipped with a CellQuest software. Voltage and fluorescence compensation adjustments are performed before each experiment using CaliBRITE beads (Becton Dickinson, CA, USA) and the FACSComp software (Becton Dickinson, CA, USA). A minimum of 10,000 events is collected for each sample. Cells are gated to exclude cell debris and abnormally large or aggregated cells.

The results of the FACS analysis are shown in FIGS. 8A to 8C. The hCat K cells show increased fluorescence in the presence than in the absence of the substrate Z-Leu-Arg-Rho (FIG. 8A). Furthermore, the intensity of fluorescence in hCat K cells in the presence of Z-Leu-Arg-Rho is two-fold higher than in the mock cells (FIG. 8B). The increase in fluorescence seen in the hCat K cells is repressed when the cells are subjected to the inhibitor E64d (FIG. 8C).

The results of the FACS analysis further confirms and validates the use of this assay for measuring intracellular cathepsin K activity.

It is the intent of the Applicant to provide a cell-based assay for cathepsin K activity suitable for identifying inhibitors of cathepsin K. To that end a mammalian cell line stably expressing a recombinant cathepsin K is established (hCatK). The enzyme synthesized as a pre-pro enzyme is processed intracellularly to the active form and has an apparent lysosomal localization. The cell based assay measuring intracellular cathepsin K activity using the recombinant cells is achieved. Using peptide substrates conjugated to indicator molecules such as [Z-Leu-Arg]$_2$-rhodamine the assay demonstrates specificity and sensitivity for cathepsin K activity over background proteases. Therefore, utilizing the hCatK cells, a cell based screening method to identify cell permeable inhibitors of cathepsin K is provided.

What is claimed is:

1. An assay for measuring the activity of cathepsin K activity in a recombinant eukaryotic cell comprising the steps of:
   a) transforming a eukaryotic host cell with a vector having a nucleotide sequence encoding pre-pro-cathepsin K, to provide a transformed host cell;
   b) incubating said transformed host cell with a substrate to said cathepsin K; and
   c) determining said cathepsin K activity in said transformed host cell;
   wherein said eukaryotic host cell is a mammalian host cell selected from a host cell having low or no endogenous cathepsin K activity, and said selected mammalian host cell is capable of expressing and processing said pre-pro-cathepsin K to a mature and active cathepsin K enzyme; and wherein said assay is conducted in the presence of a cell-impermeable protease inhibitor which is capable of inhibiting cathepsin K activity.

2. The assay of claim 1, wherein said inhibitor is cystatin and is used at a concentration of about 0.1 to 100 µg/ml.

3. The assay of claim 2, wherein said substrate is cell permeable comprising di-or tri-peptides.

4. The assay of claim 3, wherein said substrate is a di-peptide.

5. The assay of claim 4, wherein said di-peptide substrate is selected from the group consisting of Z-Phe-Arg, Z-Leu-Arg, and mixtures thereof.

6. The assay of claim 5, wherein said substrate comprises an indicator molecule to provide a conjugated substrate.

7. The assay of claim 6, wherein said indicator molecule comprises a moiety selected from the group consisting of a radioactive compound, a fluorophore compound, a chromophore compound, and mixtures thereof.

8. The assay of claim 7, wherein said indicator molecule being a fluorophore is selected from the group consisting of rhodamine, aminomethylcoumarin (AMC), or mixtures thereof.

9. The assay of claim 8, wherein said conjugated substrate is selected from the group consisting of Z-Phe-Arg-aminometbylcoumarin, Z-Leu-Arg-aminomethylcoumarin, Z-Phe-Arg-rhodamine, (Z-Leu-Arg-rhodamine)$_2$-rhodamine, and mixtures thereof.

10. The assay of claim 9, wherein determining cathepsin K activity is by comparing said cathepsin K activity in said transformed host cell to a standard.

11. The assay of claim 10, wherein said standard is selected from the group consisting of pure cathepsin K, non-transformed cells, non-cathepsin K expressing transformed cells, and mixtures thereof.

12. A method for identifying a compound as an inhibitor of cathepsin K activity comprising the steps of:
   a) incubating an eukaryotic host cell transformed with a vector having a nucleotide sequence encoding pre-pro-cathepsin K with a substrate to cathepsin K in the presence of said compound,
   b) incubating an eukaryotic host cell transformed with a vector having a nucleotide sequence encoding pre-pro-cathepsin K with a substrate to cathepsin K in the absence of said compound, and
   c) comparing said cathepsin K activity of (a) to (b);
   wherein said eukaryotic host cell is a mammalian host cell selected from a host cell having low or no endogenous cathepsin K activity, and said selected mammalian host cell is capable of expressing and processing said pre-pro-cathepsin K to a mature and active cathepsin K enzyme; and
   wherein said assay is conducted in the presence of cystatin used at a concentration of about0.1 to 100 µg/ml.

13. The method of claim 12, wherein said substrate is cell permeable comprising di- or tri-peptides.

14. The method of claim 13, wherein said substrate is a di-peptide.

15. The method of claim 14, wherein said di-peptide substrate is selected from the group consisting of Z-Phe-Arg, Z-Leu-Arg, and mixtures thereof.

16. The method of claim 15, wherein said substrate comprises an indicator molecule to provide a conjugated substrate.

17. The method of claim 16, wherein said indicator molecule comprises a moiety selected from the group consisting of a radioactive compound, a fluorophore compound, a chromophore compound, and mixtures thereof.

18. The method of claim 17, wherein said indicator molecule being a fluorophore is selected from the group consisting of rhodamine, aminomethylcoumarin (AMC), and mixtures thereof.

19. The method of claim 18, wherein said conjugated substrate is selected from the group consisting of Z-Phe-Arg-aminomethylcoumarin, Z-Leu-Arg-aminomethylcoumarin, Z-Phe-Arg-rhodamine, Z-Leu-Arg-rhodamine, (Z-Leu-Arg-rhodamine)$_2$-rhodamine, and mixtures thereof.

20. The method of claim 19, wherein activity of said cathepsin K on said conjugated substrate is measured by fluorescent light emission.

21. An assay kit for measuring intracellular cathepsin K activity in a mammalian host cell comprising:

a) a host cell transfected with a recombinant vector comprising a nucleotide sequence encoding pre-pro-cathepsin K;

b) a positive control reagent for said cathepsin K activity;

c) a negative control reagent for said cathepsin K activity;

d) a substrate for said cathepsin K activity conjugated to an indicator molecule in an appropriate solution; and e) a cell impermeable protease inhibitor, which is capable of inhibiting cathepsin K activity, in an appropriate solution.

* * * * *

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: PCR PRIMER

<400> SEQUENCE: 1
acagatttcc atcagcag                                                   18

<210> SEQ ID NO 2
<211> LENGTH: 18
<212> TYPE: DNA
<213> ORGANISM: Artificial Sequence
<220> FEATURE:
<223> OTHER INFORMATION: PCR PRIMER
```

```
<400> SEQUENCE: 2
agtaggaagg atcatttg                                               18

<210> SEQ ID NO 3
<211> LENGTH: 34
<212> TYPE: DNA
<213> ORGANISM: Artificial Sequence
<220> FEATURE:
<223> OTHER INFORMATION: PCR PRIMER

<400> SEQUENCE: 3
gaagccagac gaattcacag atttccatca gcag                             34

<210> SEQ ID NO 4
<211> LENGTH: 50
<212> TYPE: DNA
<213> ORGANISM: Artificial Sequence
<220> FEATURE:
<223> OTHER INFORMATION: PCR PRIMER

<400> SEQUENCE: 4
attagtcttg cggccgcgga tcctcacatc ttggggaagc tggccaggtt            50
```